(12) United States Patent
Ferrari et al.

(10) Patent No.: US 7,393,974 B2
(45) Date of Patent: Jul. 1, 2008

(54) PROCESS FOR THE PREPARATION OF 1-(AMINOMETHYL) CYCLOHEXANEACETIC ACID

(75) Inventors: Massimo Ferrari, Cenate Sotto (IT); Marcello Ghezzi, Curno (IT); Paolo Belotti, San Paolo d'Argon (IT)

(73) Assignee: Erregierre S.p.A., San Paolo D'Argon (IT)

( * ) Notice: Subject to any disclaimer, the term of this patent is extended or adjusted under 35 U.S.C. 154(b) by 365 days.

(21) Appl. No.: 10/433,241

(22) PCT Filed: Nov. 29, 2001

(86) PCT No.: PCT/EP01/13953

§ 371 (c)(1), (2), (4) Date: Nov. 13, 2003

(87) PCT Pub. No.: WO02/44123

PCT Pub. Date: Jun. 6, 2002

(65) Prior Publication Data

US 2005/0049432 A1 Mar. 3, 2005

(30) Foreign Application Priority Data

Dec. 1, 2000 (IT) .......................... MI2000A2608

(51) Int. Cl.
C07C 61/08 (2006.01)
A61K 31/195 (2006.01)

(52) U.S. Cl. ...................................... 562/507; 514/561
(58) Field of Classification Search ................ 562/507; 514/561

See application file for complete search history.

(56) References Cited

U.S. PATENT DOCUMENTS

| 4,024,175 | A | 5/1977 | Satzinger |
| 4,960,931 | A | 10/1990 | Butler |
| 5,068,413 | A | 11/1991 | Steiner |
| 6,255,526 | B1 * | 7/2001 | Pesachovich et al. ....... 562/507 |

FOREIGN PATENT DOCUMENTS

WO    WO 98/28255    *    7/1998

OTHER PUBLICATIONS

Grant et al , chemical dictionary , 1987, p. 220.*

* cited by examiner

*Primary Examiner*—Taylor Victor Oh
(74) *Attorney, Agent, or Firm*—Stetina Brunda Garred & Brucker

(57) ABSTRACT

A conversion process of gabapentin hydrochloride into gabapentin comprising: a) dissolution of gabapentin hydrochloride in a solvent in which the gabapentin hydrochloride and the gabapentin are completely soluble; and b) subsequent addition of an amine that allows the removal of the chloride ion from the solution containing gabapentin hydrochloride, by precipitation of the hydrochloride of the same amine, leaving the gabapentin in solution in free amino acid form.

5 Claims, No Drawings

PROCESS FOR THE PREPARATION OF 1-(AMINOMETHYL) CYCLOHEXANEACETIC ACID

FIELD OF THE INVENTION

The present invention concerns a preparation process of 1-(aminomethyl) cyclohexaneacetic acid (GABAPENTIN).

PRIOR ART

GABAPENTIN, characterized by the following structural formula (I)

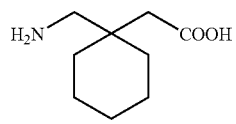

(I)

is an active principle mainly used in human therapy for the treatment of cerebral disease, namely epilepsy ("Drugs of the future", vol. 9, N° 6, 1984, pp. 418-419). Various processes are described in the art for the synthesis of this molecule. The American patent U.S. Pat. No. 4,024,175 describes the preparation of GABAPENTIN starting from its hydrochloride salt, by treatment of an aqueous solution of the latter with ion exchange resins, so as to remove the chloride ion and make the GABAPENTIN molecule available in a free amino acid form. The solution obtained at the end of the treatment is concentrated by distillation and the residue is recovered with alcohols to allow the isolation of GABAPENTIN. However, this process is complex and difficult, particularly due to the specific plant engineering technology necessary to remove the chloride ion and make GABAPENTIN available in a free amino acid form.

The WO patent 98/28255 contains a description for the preparation of GABAPENTIN starting with its hydrochloride salt, in which elimination of the chloride ion is achieved in a different way from that described in the previous patent. After having solubilized GABAPENTIN HYDROCHLORIDE in suitable non-aqueous solvents, an amine is added to the resultant solution which salifies the chloride ion, making it soluble, and thus allowing the precipitation of GABAPENTIN in a new polymorphic form called "FORM III", which differs from the polymorphic form known as "FORM II", which is that most widely used and sold. The GABAPENTIN obtained in the polymorphic form known as "FORM III", is necessarily transformed into the polymorphic form "FORM II" by treatment with alcohols. In addition, this treatment has the disadvantage of not being able to recover the used amine and recycle it in the salification stage of the chloride ion. Therefore the need was felt for a preparation process of GABAPENTIN in the polymorphic form "FORM II", that of greatest use and commercial diffusion, starting with GABAPENTIN HYDROCHLORIDE, able to overcome the technical drawbacks connected with the need to use facilities for ion exchange resins, and able to avoid passing through a polymorphic form "FORM III" of GABAPENTIN, different from the one on the market.

SUMMARY

A new separation process of GABAPENTIN in the polymorphic form "FORM II", has now been found, starting with GABAPENTIN HYDROCHLORIDE, capable of overcoming technical drawbacks and those connected with the need to pass through an unusable crystalline form on sale, typical of the processes known in the art.

The applicant has unexpectedly and surprisingly found a new separation process of GABAPENTIN in the polymorphic form "FORM II", starting with GABAPENTIN HYDROCHLORIDE, in which the chloride ion is eliminated by precipitating it as an insoluble salt, releasing GABAPENTIN in solution in free amino acid form.

DETAILED DESCRIPTION OF THE INVENTION

A conversion process of gabapentin hydrochloride into gabapentin therefore constitutes a purpose of the present invention comprising:

a) dissolution of gabapentin hydrochloride in a solvent in which the gabapentin hydrochloride and the gabapentin are completely soluble; and b) subsequent addition of an amine that allows the removal of the chloride ion from the solution containing gabapentin hydrochloride, by precipitation of the hydrochloride of the same amine, releasing gabapentin in solution in free amino acid form.

The solvent used at stage a) to completely solubilize gabapentin hydrochloride is preferably an aqueous solvent, more preferably a solvent consisting of at least 50% by weight of water, more preferably the solvent consists of at least 70% by weight of water, more preferably the solvent consists of at least 90% by weight of water, still more preferably the solvent is water.

The amine used at stage b) to remove the chloride ion is preferably an amine with cycloalkyl or aryl substituents, more preferably it is selected from the group consisting of monocyclohexylamine, dicyclohexylamine, dibenzylamine, tricyclohexylamine, or their mixtures, still more preferably it is dicyclohexylamine.

The dissolution at stage a) is carried out at a temperature which depends on the solvent used and such as to allow the complete dissolution of gabapentin hydrochloride and gabapentin, the temperature is preferably between 10° and 90° C., more preferably between 20° and 70° C., still more preferably between 30° and 50° C.

One of the particularly preferred embodiments of the conversion process of gabapentin hydrochloride into gabapentin, according to the present invention, comprises, in addition to stages a) and b) as above, the removal stage c) by filtering the precipitate of the amine hydrochloride, from the solution containing gabapentin in free amino acid form, and the recovery of the amine by the alkali treatment of the amine hydrochloride to give the free amine which is recycled at stage b).

An additional preferred embodiment of the process, according to the present invention comprises, in addition to stages a), b) and c), as above, also stage d) wherein the solution containing gabapentin in free amino acid form is concentrated by distillation and the residue is recovered with alcohols selected from the group consisting of alkyl alcohols with one to four linear or branched carbon atoms, or their mixtures, preferably ethyl alcohol, to give the isolation of gabapentin in polymorphic form "FORM II".

An additional preferred embodiment of the present invention comprises, in addition to the stages a), b), c) and d), also stage e) wherein gabapentin in polymorphic form "FORM II", isolated at stage d), is purified by treatment with alcohol selected from the group consisting of alkyl alcohols with one to four linear or branched carbon atoms, or their mixtures, preferably a methyl alcohol/isopropyl alcohol mixture.

More particularly, according to the present invention, formula (II) gabapentin hydrochloride is used as a process intermediate

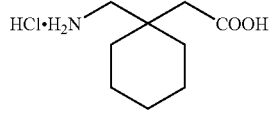

(II)

prepared due to the well known "Hoffmann rearrangement" reaction; this reaction consists in making the formula (III) compound react

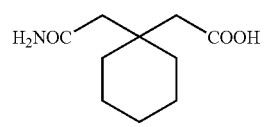

(III)

with sodium or potassium hypochlorite, or sodium or potassium hypobromite to give an intermediate isocyanate that, because of the subsequent rearrangement, leads to the formation of gabapentin, isolated as a hydrochloride by acidification of the reaction environment with hydrochloric acid. The intermediate of formula (II) gabapentin hydrochloride is completely solubilized in aqueous solvent, in this case water, and an amine is added to the solution obtained, in this case, dicyclohexylamine of formula (IV)

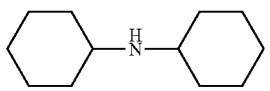

(IV)

able to move the chloride ion from gabapentin, it being salified; the dicyclohexylamine hydrochloride of formula (V) thus formed

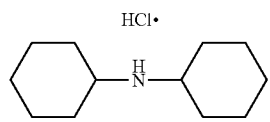

(V)

is insoluble in aqueous environment, while gabapentin, thus rendered available in free amino acid form, vice versa proves soluble in this environment.

The suspension obtained is filtered recovering, on the one hand, an aqueous solution containing gabapentin in a free amino acid form and, on the other, a solid (cake) of amine hydrochloride, in this case, dicyclohexylamine hydrochloride, which treated with strong bases, preferably hydroxides of alkaline metals, more preferably sodium hydroxide, thus allows the recovery of the amine, in this case, the dicyclohexylamine, and its recycling. The aqueous solution containing gabapentin is concentrated by distillation until the start of precipitation, with the residue taken back with an alkyl alcohol, in this case ethanol. The suspension obtained is filtered, resulting in gabapentin in the polymorphic form "FORM II", with content of impurity of formula (VI)

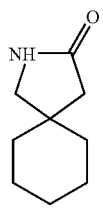

(VI)

of less than 0.05% by weight.

The process, subject of the present invention, also has the advantage that any presence of gabapentin hydrochloride or amine, in this case dicyclohexylamine, in the aqueous solution obtained after the removal of amine hydrochloride, in this case dicyclohexylamine hydrochloride, is absent in the alcoholic mother waters from which gabapentin is isolated in the polymorphic form "FORM II".

The raw gabapentin obtained is treated under reflux with alcohol selected from the group consisting of alkyl alcohols with one to four carbon atoms, linear or branched, or their mixtures, preferably a methyl alcohol/isopropyl alcohol mixture, and the suspension thus obtained is brought to 0° C. and filtered, obtaining gabapentin with polymorphic form "FORM II", verified by FTIR and X-Ray analyses, and having a HPLC purity in excess of 99.9%.

Below are some illustrative, but non-limiting examples of the present invention.

EXAMPLE 1

100 g of gabapentin hydrochloride are solubilized in 500 g of deionized water and 90 g of dicyclohexylamine are added while heating to 30°-50° C. An abundant precipitation of dicyclohexylamine hydrochloride is produced that is filtered with a Buchner funnel. The dicyclohexylamine hydrochloride solid is treated with sodium hydroxide, thus regaining the dicyclohexylamine that is thus recovered and recycled in the separation stage of the chloride ion by precipitation, while the aqueous solution contains gabapentin in free amino acid form.

The aqueous solution obtained by filtering is distilled under reduced pressure, until the start of precipitation, and the residue is taken back with ethyl alcohol, heated to 40°-50° C., and the suspension obtained is cooled for a few hours and filtered.

The solid obtained is vacuum dried at 30°-40° C., producing raw gabapentin in the polymorphic form "FORM II" with a formula (VI) impurity content of less than 0.05%. The yield is 80%.

EXAMPLE 2

50 g of raw gabapentin arising from example 1 are suspended in 250 g of methyl alcohol and 125 g of isopropyl alcohol. It is heated under reflux for 30 minutes, and cooled at 20-25° C. for two hours and subsequently at 0° C. for a further two hours. The suspension is filtered with a Buchner funnel and is vacuum dried at 30°-40° C., producing gabapentin of polymorphic form "FORM II" with a HPLC purity greater than 99.85%.

The invention claimed is:

1. A conversion process of gabapentin hydrochloride into gabapentin form (II) comprising:
   a) dissolution of gabapentin hydrochloride in water in which the gabapentin hydrochloride and the gabapentin are completely soluble;
   b) subsequent addition of an amine selected from the group consisting of: monocyclohexylamine, dicyclohexylamine, dibenzylamine and tricyclohexylamine, that allows the removal of the chloride ion from the solution containing gabapentin hydrochloride, by precipitation of the hydrochloride of the same amine, leaving gabapentin in solution in free amino acid form;
   (c) removing the precipitated amine hydrochloride salt from the solution containing gabapentin of step b) by filtration; and
   d) concentrating by distillation the aqueous solution containing gabapentin in free amino acid form coming from step (c) and taking the residue with an alcohol selected from the group consisting of linear or branched alkyl alcohols with one to four carbon atoms or mixtures thereof, thereby obtaining the precipitation of raw gabapentin in polymorphic Form II and isolating gabapentin form (II) by filtration;
   e) further purifying the raw gabapentin isolated in step (d) by treatment with an alcohol selected from the group consisting of linear or branched alkyl alcohols with one to four carbon atoms and mixture thereof.

2. The process according to claim 1, wherein the amine is dicyclohexylamine.

3. The process according to claim 1, wherein the hydrochloride amine salt separated by filtration in step (c) is treated with alkalis thereby obtaining the starting amine which is recycled at step (b).

4. The process according to claim 1 wherein said alcohol in step (d) is ethyl alcohol.

5. The process according to claim 1, wherein said alcohol in step e) is a mixture of methyl alcohol and isopropyl alcohol.

* * * * *